(12) United States Patent
Colman et al.

(10) Patent No.: US 9,987,452 B2
(45) Date of Patent: Jun. 5, 2018

(54) VENTILATION ANALYSIS AND MONITORING

(75) Inventors: Joshua Lewis Colman, Jerusalem (IL); Zion Botesazan, D.N. Mizrach Binyamin (IL)

(73) Assignee: ORIDION MEDICAL 1987 LTD., Jerusalem (IL)

(*) Notice: Subject to any disclaimer, the term of this patent is extended or adjusted under 35 U.S.C. 154(b) by 722 days.

(21) Appl. No.: 12/999,111

(22) PCT Filed: Jun. 30, 2009

(86) PCT No.: PCT/IL2009/000651
§ 371 (c)(1),
(2), (4) Date: Dec. 15, 2010

(87) PCT Pub. No.: WO2010/001390
PCT Pub. Date: Jan. 7, 2010

(65) Prior Publication Data
US 2011/0105935 A1 May 5, 2011

Related U.S. Application Data

(60) Provisional application No. 61/129,474, filed on Jun. 30, 2008.

(51) Int. Cl.
*A61B 5/08* (2006.01)
*A61M 16/10* (2006.01)
(Continued)

(52) U.S. Cl.
CPC ......... *A61M 16/1005* (2014.02); *A61B 5/087* (2013.01); *A61B 5/0836* (2013.01);
(Continued)

(58) Field of Classification Search
CPC .... A61M 2230/432; A61B 5/087; A61B 5/08; A61B 5/0816; A61B 5/082; A61B 5/7267; A61B 5/7235
(Continued)

(56) References Cited

U.S. PATENT DOCUMENTS 4,423,739 A 1/1984 Passaro
5,129,401 A 7/1992 Corenman
(Continued)

FOREIGN PATENT DOCUMENTS

DE 2812379 9/1979
GB 2409951 7/2005

OTHER PUBLICATIONS

Jaffe (2002) Volumetric capnography—the next advance in CO2 monitoring. Technical report Jan. 2002 Rev. 04, Dec. 2, 2002 (Dec. 2, 2002), pp. 1-21, XP055013972 retrieved from the internet on Dec. 6, 2011.

(Continued)

*Primary Examiner* — Patricia Mallari
*Assistant Examiner* — Karen Toth

(57) ABSTRACT

A ventilation analysis system comprising an interface module adapted to receive a carbon dioxide (CO2) signal and a breath flow dynamics signal, and control logic adapted to produce a ventilation indicator, based on a mutual analysis of the CO2 signal and the breath flow dynamics signal. The ventilation indicator may be, for example, an estimated CO2 waveform, an End-Tidal CO2 (ETCO2) value, and/or a minute CO2 value.

23 Claims, 4 Drawing Sheets

(51) Int. Cl.
    *A61B 5/083*  (2006.01)
    *A61B 5/087*  (2006.01)
    *A61M 16/00*  (2006.01)

(52) U.S. Cl.
    CPC ... *A61M 16/0003* (2014.02); *A61M 2016/003* (2013.01); *A61M 2016/103* (2013.01); *A61M 2205/3334* (2013.01); *A61M 2205/583* (2013.01); *A61M 2230/432* (2013.01)

(58) Field of Classification Search
    USPC .................................................. 600/529–543
    See application file for complete search history.

(56)                References Cited

U.S. PATENT DOCUMENTS

| 6,015,388 | A  | * | 1/2000  | Sackner et al. ............... 600/529 |
| 6,099,481 | A  |   | 8/2000  | Daniels |
| 6,435,182 | B1 | * | 8/2002  | Lutchen et al. ......... 128/204.21 |
| 6,898,452 | B2 | * | 5/2005  | Al-Ali et al. ................. 600/323 |
| 2003/0100843 | A1 | * | 5/2003  | Hoffman ...................... 600/538 |
| 2005/0188991 | A1 | * | 9/2005  | Sun et al. ................ 128/204.23 |
| 2005/0245836 | A1 | * | 11/2005 | Star et al. ..................... 600/532 |
| 2005/0284476 | A1 | * | 12/2005 | Blanch .................. A61M 16/00 128/204.21 |
| 2006/0107755 | A1 | * | 5/2006  | Kuo et al. ................... 73/861.23 |
| 2007/0000494 | A1 | * | 1/2007  | Banner ................ A61B 5/0205 128/204.23 |
| 2007/0123792 | A1 |   | 5/2007  | Kline |
| 2007/0232951 | A1 | * | 10/2007 | Euliano et al. ............... 600/538 |
| 2007/0249950 | A1 | * | 10/2007 | Piaget et al. ................. 600/529 |
| 2008/0135044 | A1 | * | 6/2008  | Freitag et al. ........... 128/200.26 |

OTHER PUBLICATIONS

Breen and Jacobsen (1997) Carbon dioxide spirogram (but not capnogram) detects leaking inspiratory valve in a circle circuit. Anesthesia and Analgesia 85(6): 1372-1376.

* cited by examiner

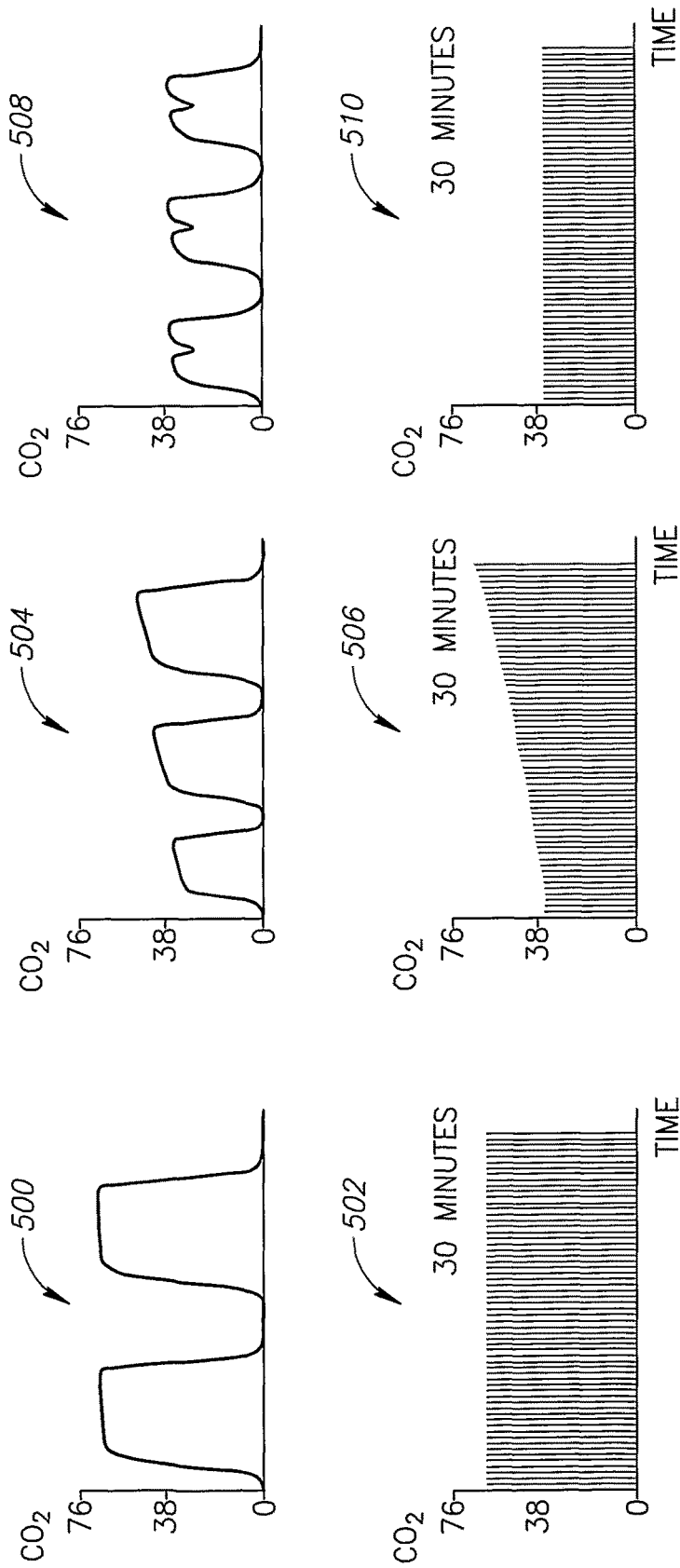

VENTILATION ANALYSIS AND MONITORING

CROSS REFERENCE TO RELATED APPLICATIONS

This application is the U.S. National Stage of PCT/IL2009/000651, filed Jun. 30, 2009, which claims the benefit of U.S. Provisional Patent Application No. 61/129,474, filed Jun. 30, 2008 and entitled "Ventilation Analysis and Monitoring", the entirety of each of which is incorporated herein by reference.

FIELD

Embodiments of the disclosure relate to ventilation analysis and monitoring in patients.

BACKGROUND

Capnography is often defined as the measurement of the level of carbon dioxide ($CO_2$) in exhaled and/or inhaled breath. Since infrared light was found to be absorbed particularly well by $CO_2$, capnographs usually measure infrared absorption in the breath gasses, which indicates the level of $CO_2$ in these gasses. Other measurement technologies exist as well.

The information obtained from a capnographic measurement is sometimes presented as a series of waveforms, representing the partial pressure of $CO_2$ in the patient's exhaled breath as a function of time.

Clinicians commonly use capnography in order to assess a patient's ventilatory status. Respiratory arrest and shunt may be speedily diagnosed, and a whole range of other respiratory problems and conditions may be determined by the capnographic measurement. Capnography is considered to be a prerequisite for safe intubation and general anesthesia, as well as for correct ventilation management.

Breath flow dynamics is another ventilation-related factor that is sometimes being measured. Whereas capnography is usually indicative of physiological aspects of ventilation, breath flow dynamics measurement is often indicative of the mechanics of respiration—the inhalation and exhalation activity of patient's lungs.

SUMMARY

There is provided, according to embodiment, a ventilation analysis system comprising: an interface module adapted to receive a carbon dioxide ($CO_2$) signal and a breath flow dynamics signal; and control logic adapted to produce a ventilation indicator, based on a mutual analysis of said $CO_2$ signal and said breath flow dynamics signal.

There is further provided, according to an embodiment, a method for ventilation analysis, the method comprising: receiving a $CO_2$ signal and a breath flow dynamics signal; and mutually analyzing the $CO_2$ signal and the breath flow dynamics signal, to produce a ventilation indicator.

In some embodiments, said ventilation indicator comprises an estimated $CO_2$ waveform, an End-Tidal $CO_2$ (EtCO$_2$) value and/or a minute $CO_2$ value.

In some embodiments, the system further comprises a $CO_2$ sensor adapted to produce said $CO_2$ signal.

In some embodiments, said $CO_2$ sensor comprises a wireless $CO_2$ sensor.

In some embodiments, said $CO_2$ sensor comprises a $CO_2$ sensor having a response time of 100 milliseconds (ms) or more, 500 ms or more and/or 900 ms or more.

In some embodiments, the system further comprises a breath flow dynamics sensor adapted to produce said breath flow dynamics signal.

In some embodiments, said breath flow dynamics sensor comprises a wireless breath flow dynamics sensor.

In some embodiments, said breath flow dynamics sensor comprises a flow sensor, an acoustic sensor, a thermal sensor, a chest movement detector, a computer-aided video analyzer and/or a Doppler radar.

In some embodiments, said interface module is further adapted to receive a Saturation of Peripheral Oxygen (SpO$_2$) signal.

In some embodiments, the system further comprises an SpO$_2$ sensor adapted to produce said SpO$_2$ signal.

In some embodiments, the receiving of the $CO_2$ signal comprises wirelessly receiving the $CO_2$ signal.

In some embodiments, the $CO_2$ signal comprises discrete Partial Pressure $CO_2$ (PCO$_2$) readings taken every 100 ms or more, every 500 ms or more and/or every 900 ms or more.

In some embodiments, the receiving of the breath flow dynamics signal comprises wirelessly receiving the breath flow dynamics signal.

In some embodiments, the breath flow dynamics signal comprises a flow measurement, an acoustic measurement, a thermal measurement, a chest movement measurement, a computer-aided video analysis and/or a Doppler radar signal.

In some embodiments, the method further comprises receiving an SpO$_2$ signal.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIGS. 5A-C schematically show capnogram patterns.

DETAILED DESCRIPTION

Figure 1:
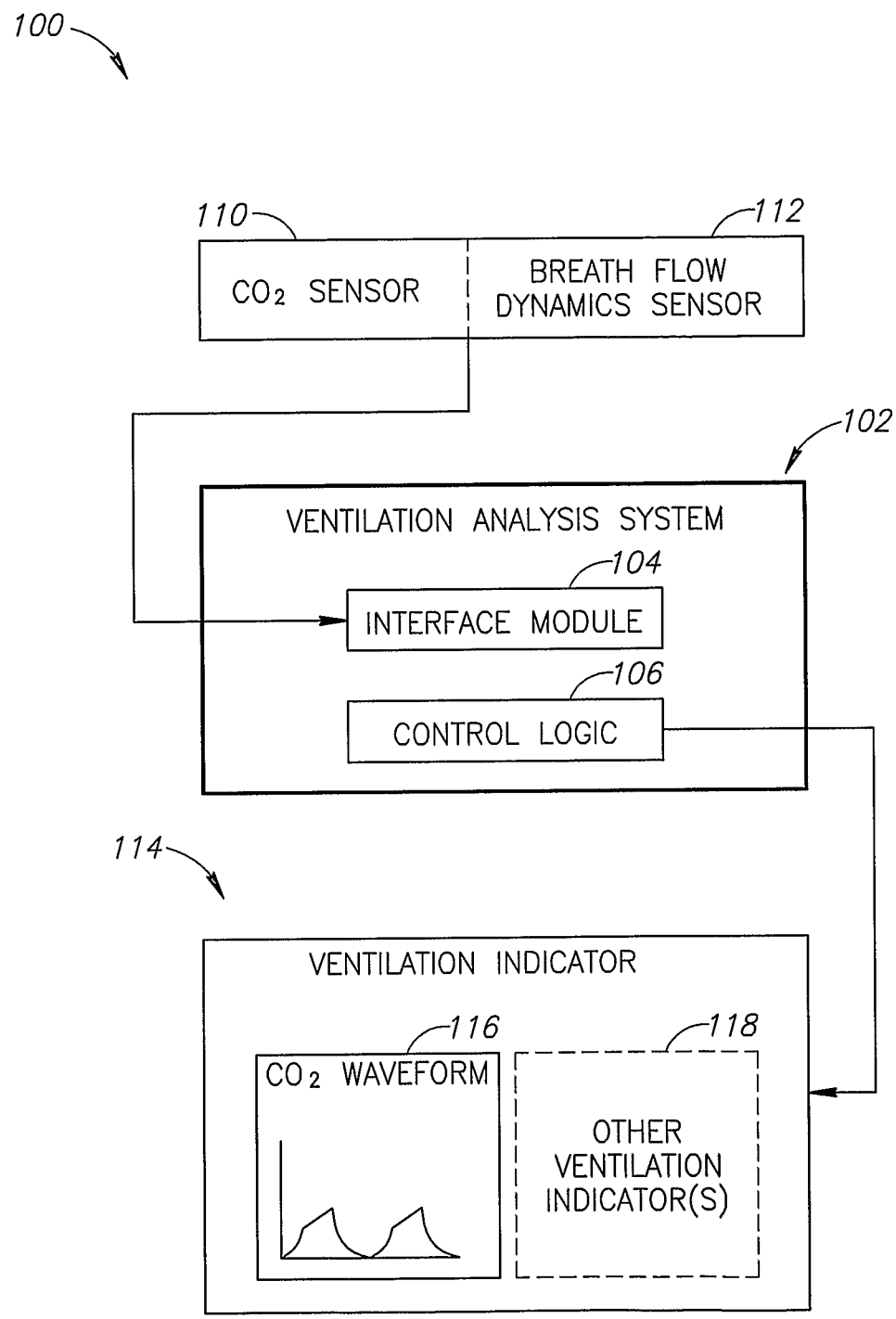
FIG. 1 schematically shows a block diagram of a ventilation analysis system.

An aspect of some embodiments of the disclosure relates to a ventilation analysis and/or monitoring system. The system may be adapted to interface with one or more sensors to receive a carbon dioxide ($CO_2$) signal and a breath flow dynamics (hereinafter "BFD") signal, both pertaining to a patient. The received signals may be mutually analyzed, to produce a ventilation indicator that may assist a clinician in assessing the patient's ventilatory condition.

Advantageously, the $CO_2$ signal may be received from a $CO_2$ sensor adapted to operate with a relatively slow response time. In some embodiments, this may enable the use of a relatively small, power efficient and/or simple sensor, compared to conventional $CO_2$ sensors commonly used today in conjunction with capnographs. Various $CO_2$ sensors are being constantly introduced to the market, where one of the major improvements these sensors offer is faster and faster response times. Response time is often defined as the duration between two consecutive samples taken by the $CO_2$ sensor. For example, a sensor having a response time of 50 milliseconds (ms), is able to measure (or "read") momentary breath $CO_2$ concentration once every 50 ms, which amounts to 20 measurements per second. A faster response time means a shorter response time and therefore more measurements per second.

Generally, faster response times enable the creation of a $CO_2$ waveform (or "graph") having a greater resolution. A $CO_2$ waveform is a graphic representation of the breath $CO_2$ concentration over time, which is sometimes displayed by capnographs. If more $CO_2$ readings are available per a unit of time, the resolution of the waveform increases, and so does its accuracy and the amount of meaningful information it may relay to a clinician. Therefore, newly-introduced capnographs often aim to offer faster response times than before. However, there is often a tradeoff between response time and factors like manufacturing complexity, power consumption, physical size and weight, cost and/or the like.

Therefore, in an embodiment, the ventilation analysis and/or monitoring system is advantageously adapted to provide a clinically-meaningful ventilation indication while utilizing a $CO_2$ sensor having a relatively slow response time, such as a response time in the range of 100-300 ms, 300-500 ms, 500-700 ms, 700-900 ms, 900-1100 ms or above 1100 ms. This may enable the use of a relatively simple, small, low power, lightweight and/or otherwise more cost-effective $CO_2$ sensor. In other embodiments, a $CO_2$ sensor may nonetheless have a relatively fast response time, such as a response time of below 100 ms.

The ventilation analysis and/or monitoring system may provide the ventilation indication by pairing a signal received from the $CO_2$ sensor with a signal received from a BFD sensor. BFD, which is often indicative of the mechanics of respiration—the inhalation and exhalation activity of patient's lungs, may be measured using various methods known in the art. For example, a flow sensor is sometimes positioned about the patient's nostrils or mouth, directly measuring the dynamics of inward and/or outward gas flow. If the patient is intubated and given artificial respiration, a measurement of the BFD may be provided by the respirator.

Measurement of BFD may also be performed essentially indirectly, such as using an acoustic sensor sensitive to sound emitted during respiration, a thermal sensor sensitive to temperature changes during respiration, a chest movement detector attached to the patient's body, a microwave Doppler radar system adapted to produce a signal indicative of chest movement and/or a computer-aided video analyzer adapted to visually recognize chest movement.

BFD may provide information such as a numerical respiration rate value and/or a visual indication of exhalation/inhalation cycles over a time axis. A respiration rate is often defined as the number of exhalation/inhalation cycles per minute, and is commonly considered a clinical parameter of great importance. A visual indication may include a graph showing the exhalation/inhalation spread over a time axis.

Reference is now made to FIG. 1, which shows a block diagram 100 of a ventilation analysis and/or monitoring system (hereinafter "system") 102, in accordance with an embodiment. System 102 may be essentially what is often referred to as a capnograph, or be incorporated within a capnograph.

System 102 may include an interface module 104 adapted to interface with a $CO_2$ sensor 110 and with a BFD sensor 112, which measure breath $CO_2$ concentration and BFD, respectively, of a patient. The interface with each of $CO_2$ sensor 110 and BFD sensor 112 may be wired or wireless. Optionally, $CO_2$ sensor 110 and BFD sensor 112 are enclosed within a single physical unit, which may be referred to as a multi-purpose sensor adapted to sense both $CO_2$ and BFD.

Interface module 104 may further be adapted to interface with an $SpO_2$ sensor (not shown), to receive an $SpO_2$ signal.

Interface module 104 may periodically receive a $CO_2$ signal from $CO_2$ sensor 110 and a BFD signal from BFD sensor 112, and make these signals available to a control logic 106. Control logic 106 may mutually analyze the $CO_2$ and BFD signals, and output (or "produce") one or more ventilation indicator(s) 114 based on both signals.

An example of a ventilation indicator is a $CO_2$ waveform 116. As mentioned, conventional capnographs may require a fast-response $CO_2$ sensor in order to produce a $CO_2$ waveform of a sufficiently high resolution. Nonetheless, $CO_2$ waveform 116 may be produced based on the BFD signal and on the $CO_2$ signal which may be of a slow-response $CO_2$ sensor. The creation of $CO_2$ waveform 116 is further discussed below.

In addition to $CO_2$ waveform 116, other ventilation indicator(s) 118 may be created from the mutual analysis of the BFD and $CO_2$ signals. For example, a ventilation indicator may be end-tidal $CO_2$ ($EtCO_2$), minute $EtCO_2$ and/or the like. These ventilation indicators are further discussed below.

System 102 may be further adapted to relay to a clinician, visually and/or sonically, $SpO_2$ values derived from the received $SpO_2$ signal.

System 102 may be embodied in a computerized device having input, output and processing abilities to carry out operations of interface module 104 and control logic 106. For example, system 102 may be an essentially stationary computerized device positioned next to a patient's hospital bed or at a central location in the hospital (if remote monitoring of a patient is desired). As another example, system 102 may be an essentially mobile computerized device adapted to be carried by an emergency clinician, in an ambulance and/or the like. A patient whose ventilatory condition is desired to be monitored may be connected to $CO_2$ sensor 110 and BFD sensor 112, which transmit their readings to system 102 for analysis. The output of system 102, namely—ventilation indicator 114, may be relayed to the clinician by way of visual display on a monitor, sonic indication and/or the like.

In an embodiment, system 102, or another system (not shown) adapted to receive $CO_2$ and BFD signals, may provide a ventilation indicator or different ventilatory status having enhanced reliability. The enhanced reliability may be achieved since $CO_2$ and BFD are two measures of essentially the same system—the body ventilatory system. Each of these measures offers a different perspective of essentially the same bodily system, and therefore these measures complement each other. Monitoring both measures may allow the filtering out of issues such as false or poor readings arriving from one of the two sensors due to a defect or an error, and/or cases in which the patient is talking, eating, coughing and the like and therefore temporarily exhibiting irregular $CO_2$ and/or BFD signals.

Figure 2:
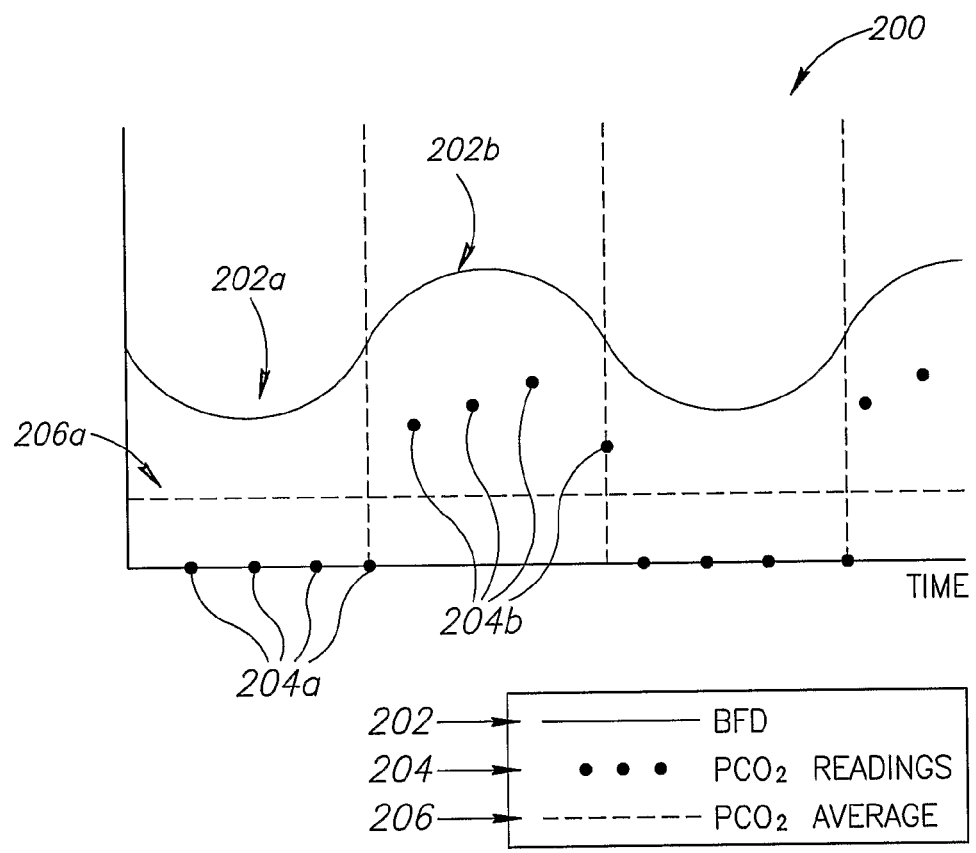
FIG. 2 schematically shows a graph of $CO_2$ and breath flow dynamics signals.

Reference is now made to FIG. 2, which shows a graph 200 of exemplary signals that may be transmitted from $CO_2$ sensor 110 and BFD sensor 112 to interface module 104 (FIG. 1).

A BFD signal 202 may indicate a respiratory state of the patient, such as whether the patient is currently exhaling or inhaling, and/or the intensity of the exhaling/inhaling at any particular moment. For example, a concave shape 202a of BFD signal 202 may be indicative of inhalation, whereas a convex shape 202b of the BFD signal may be indicative of exhalation.

A partial pressure $CO_2$ ($PCO_2$) signal, shown as discrete $PCO_2$ readings 204, may indicate one or more physiological aspects of ventilation. Horizontal distances between $PCO_2$ readings 204 may be dictated by a response time of the sensor that performed the reading. Since $PCO_2$ during inhalation is zero, zero readings 204a may be present during the inhalation. Other readings 204b, usually higher than zero, may be present during exhalation.

A $PCO_2$ average signal 206 may show an average of $PCO_2$ over time. A $CO_2$ sensor may average $PCO_2$ readings it performs, producing $PCO_2$ average signal 206, by using a capacitor and/or similar electronic means. $PCO_2$ average signal 206 is shown in the figure as a straight line 206a, for illustrative purposes only.

A $CO_2$ sensor may transmit either $PCO_2$ readings 204, $PCO_2$ average signal 206, or both.

Figure 3:
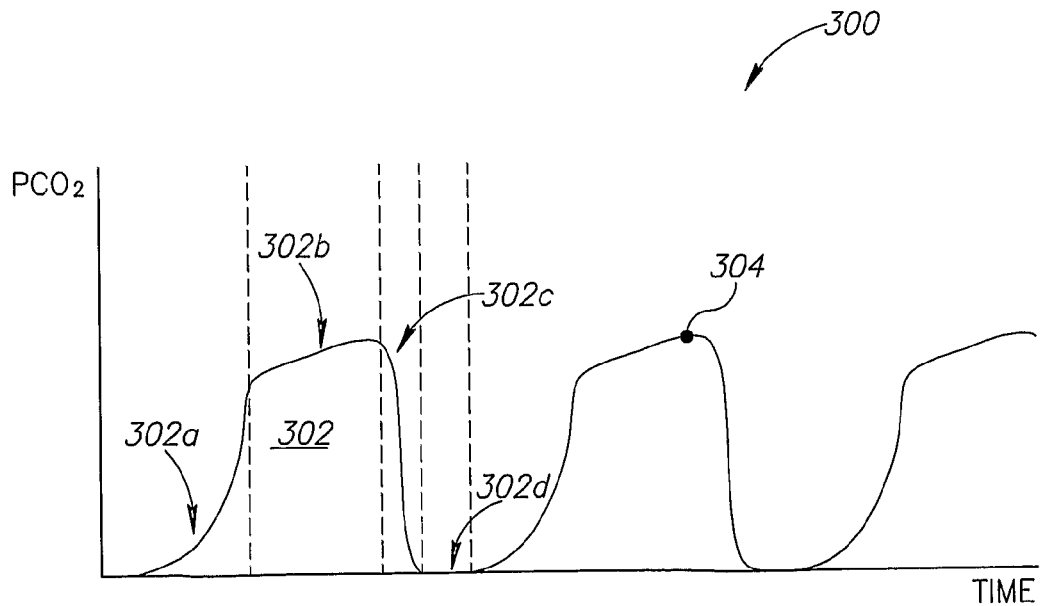
FIG. 3 schematically shows an estimated $CO_2$ waveform.

Reference is now made to FIG. 3, which shows an exemplary estimated $CO_2$ waveform 300, which is optionally the ventilation indicator produced by the ventilation analysis and/or monitoring system. The exemplary estimated $CO_2$ waveform 300, like common $CO_2$ waveforms, may contain trapezoid-like shapes, such as trapezoid 302. An upsurge curve 302a of trapezoid 302 indicates a beginning of an exhalation, a gradually rising curve 302b indicates a central part of the exhalation, and a drop curve 302c indicates an ending of the exhalation. A zero-value curve 302d indicates an inhalation.

Those of skill in the art will recognize that the shape of the trapezoids usually changes according to the medical condition of the patient, and that estimated $CO_2$ waveform 300 is meant for illustrative purposes only.

In an embodiment, estimated $CO_2$ waveform 300 may be constructed by way of the mutual analysis of the $CO_2$ and BFD signals, despite the slow response time of the $CO_2$ sensor. For example, if $PCO_2$ average signal 206 (FIG. 1) is provided by the $CO_2$ sensor, it may be possible to calculate what was the $PCO_2$ during exhalation. For instance, if the average $PCO_2$ is 20, and it is known that: (a) during inhalation the $PCO_2$ is zero; and (b) the duty cycle of the exhalation and inhalation, as apparent from the BFD signal, is 50%—then the average $PCO_2$ during exhalation is 40. A trapezoid, such as trapezoid 302, may then be constructed according to a mathematical constraint that the trapezoid's average value must be 40. Another mathematical factor that may be helpful in the construction of the trapezoid is that the product of the average $PCO_2$ during exhalation (in our example, 40) and the duration of the exhalation (which may be inferred from the BFD signal) is equal to an area that should be delimited between the constructed trapezoid and the time axis.

The BFD signal may provide information pertaining to starting and ending points of the inhalations and exhalations, so that any constructed trapezoids, such as trapezoid 302, may be synchronized with breath cycles.

If discrete $PCO_2$ readings 204 (FIG. 2) are provided by the $CO_2$ sensor, a general shape of a trapezoid may be available through other readings 204b (FIG. 2). One or more methods may be employed in order to fill in the gaps between other readings 204b and enhance the resolution of the trapezoid. For example, other readings 204b (FIG. 2) may be averaged and then treated similarly to the average $PCO_2$ described above. As another example, other readings 204b (FIG. 2) may be synchronized with breath cycles provided by the BFD signal, so that a location and an estimated shape of parts like upsurge curve 302a, gradually rising curve 302b, drop curve 302c and zero-value curve 302d may be determined.

In an embodiment, the ventilation indicator is an $EtCO_2$ value. $EtCO_2$ is often defined as the partial pressure of $CO_2$ at a point in time when $CO_2$ values stop increasing and on the verge of dropping. An exemplary $EtCO_2$ point 304 is shown in FIG. 3.

The creation of $EtCO_2$ indication may be enabled, despite the slow response time of the $CO_2$ sensor, via mathematical calculation. The $EtCO_2$ may be calculated similar to the way the $CO_2$ waveform may be created, as discussed above. If an estimated shape of a trapezoid is calculated, $EtCO_2$ for each trapezoid may also be calculated.

In an embodiment, the ventilation indicator is a minute $CO_2$ value. Minute $CO_2$ is commonly referred to as the total production of $CO_2$ per minute. By correlating the BFD signal with the $PCO_2$ average or discrete readings, minute $CO_2$ may be calculated. More specifically, when using a $PCO_2$ average signal, inhalation and exhalation cycles may be used to determine the $PCO_2$ average during exhalation alone. This exhalation $PCO_2$ may then be multiplied by a respiration rate (also obtainable from the BFD signal) to output minute $CO_2$.

Figure 4:
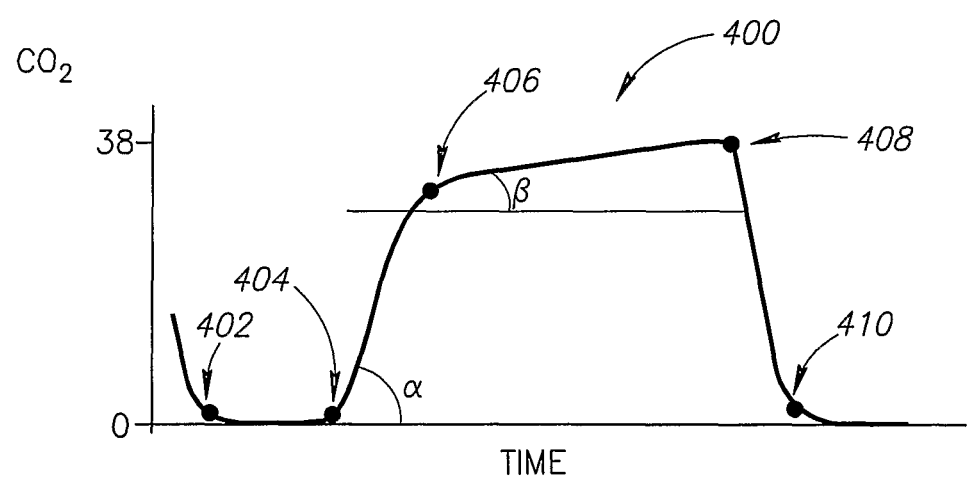
FIG. 4 schematically shows an adult normal capnogram.

Reference is now made to FIG. 4, which shows an adult normal capnogram 400 as known in the art. Adult normal capnogram 400 in spontaneously breathing subjects may be characterized by four distinct phases:

1. Dead space ventilation: Shown between points 402 and 404 in the figure, this is the earliest phase of exhalation. Physiologally, this phase corresponds to initial exhalation from upper airway (mainstem bronchi, trachea, posterior pharynx, mouth and nose).
2. Ascending phase: Shown between points 404 and 406 is a rapid rise in $CO_2$ concentration, which physiologically corresponds to alveolar gas reaching the upper airways.
3. Alveolar plateau: Shown between points 406 and 408, this is the stage where $CO_2$ reaches a generally steady state, sometimes having a mild ascending slope. Physiologally, this phase corresponds to a uniform $CO_2$ level attained in the entire breath stream.
4. Inspiratory limb: Shown between points 408 and 410 is a rapid decrease in CO2 concentration back to zero, marking the beginning of an inhalation.

Point 408, which is the intersection of the alveolar plateau and the inspiratory limb, is often referred to as the End-Tidal $CO_2$ ($EtCO_2$).

An angle $\alpha$, which designates the angle between the ascending phase curve and the X axis, is referred to as a "takeoff angle". An angle $\beta$, which designates the angle between the alveolar plateau and the X axis, is referred to as an "elevation angle".

An amplitude of capnogram 400 is dependent on $EtCO_2$ concentration. A width of capnogram 400 is dependent on expiratory time. The shape of capnogram 400 is generally rectangular, formed by almost perpendicular ascending phase (indicating absence of lower airway obstruction) and inspiratory limb (no upper airway obstruction).

Reference is now made to FIGS. 5A, 5B and 5C, which show exemplary capnogram patterns. FIG. 5A shows a capnogram 500 demonstrating elevated $EtCO_2$ with a good alveolar plateau. A corresponding graph 502 shows a 30-minute trend exhibiting a constant but elevated $EtCO_2$. Possible causes may be: (a) inadequate minute ventilation or hypoventilation; (b) respiratory depressant drugs; (c) hyperthermia, pain and/or shivering.

FIG. 5B shows a capnogram 504 demonstrating gradually increasing $EtCO_2$. A corresponding graph 506 shows a 30-minute trend exhibiting this gradual increase. Possible causes may be: (a) hypoventilation; (b) rising body temperature and/or malignant hyperthermia; (c) increased metabolism; (d) partial airway obstruction; (e) absorption of $CO_2$ from exogenous source.

FIG. 5C shows a capnogram 508 demonstrating an alveolar cleft. A corresponding graph 510 shows a 30-minute trend exhibiting constant $EtCO_2$ levels. Possible causes may be inadequate neuromuscular blockade and/or emergence from blockade.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A method for ventilation analysis, the method comprising:
   receiving discrete partial pressure ($PCO_2$) signals from a $CO_2$ sensor and breath flow dynamics (BFD) signals from a BFD sensor; wherein said $CO_2$ sensor has a response time of more than 100 ms;
   constructing, using a processor, an estimated $CO_2$ waveform by way of mutual analysis of the $PCO_2$ and BFD signals, wherein said estimated $CO_2$ waveform depicts partial pressure of $CO_2$ in exhaled breath as a function of time, and wherein constructing the estimated $CO_2$ waveform comprises
     determining a start point and an end point of exhalation and a duration of said exhalation based on said BFD signals;
     determining, based on said $CO_2$ signals, an average $PCO_2$ value obtained during the exhalation determined based on said BFD signals;
     constructing an estimated $PCO_2$ waveform based on a shape of a common $CO_2$ waveform, the determined said start point of exhalation, the determined said end point of exhalation, the determined said duration of the exhalation, and on the determined average $PCO_2$ value; and
   relaying the estimated $PCO_2$ waveform to a clinician by displaying on a display.

2. The method according to claim 1, further comprising calculating an estimated $EtCO_2$ value.

3. The method according to claim 1, further comprising calculating an estimated minute $CO_2$ value.

4. The method according to claim 1, wherein the receiving of the $CO_2$ signal comprises wirelessly receiving the $CO_2$ signal.

5. The method according to claim 1, wherein the $CO_2$ signal comprises discrete $PCO_2$ readings taken every 500 ms or more.

6. The method according to claim 1, wherein the $CO_2$ signal comprises discrete $PCO_2$ readings taken every 900 ms or more.

7. The method according to claim 1, wherein the receiving of the breath flow dynamics signal comprises wirelessly receiving the breath flow dynamics signal.

8. The method according to claim 1, wherein the breath flow dynamics signal comprises a flow measurement.

9. The method according to claim 1, wherein the breath flow dynamics signal comprises an acoustic measurement.

10. The method according to claim 1, wherein the breath flow dynamics signal comprises a thermal measurement.

11. The method according to claim 1, wherein the breath flow dynamics signal comprises a chest movement measurement.

12. The method according to claim 1, wherein the breath flow dynamics signal comprises a computer-aided video analysis.

13. The method according to claim 1, wherein the breath flow dynamics signal comprises a Doppler radar signal.

14. The method according to claim 1, further comprising receiving an $SpO_2$ signal.

15. A ventilation analysis system comprising:
   a $CO_2$ sensor configured to measure discrete partial pressure ($PCO_2$) in exhaled breath of a subject; said $CO_2$ sensor having a response time of more than 100 ms;
   a breath flow dynamics (BFD) sensor configured to measure the BFD of the subject;
   an interface module configured to receive discrete partial pressure $PCO_2$ signals from the $CO_2$ sensor and BFD signals from the BFD sensor;
   a control logic configured to receive the $PCO_2$ signals, construct an estimated $CO_2$ waveform by way of mutual analysis of the $PCO_2$ and BFD signals, wherein said estimated $CO_2$ waveform depicts partial pressure of $CO_2$ in exhaled breath as a function of time, and wherein constructing the estimated $CO_2$ waveform comprises:
     determining a start point and an end point of exhalation and a duration of said exhalation based on said BFD signals;
     determining, based on said $CO_2$ signals, an average $PCO_2$ value obtained during the exhalation determined based on said BFD signals; and
     constructing an estimated $CO_2$ waveform based on a shape of a common $CO_2$ waveform, the determined said start point of exhalation, the determined said end point of exhalation, the determined said duration of the exhalation, and on the determined average $PCO_2$ value; and
   a display configured to relay the estimated $CO_2$ waveform to a clinician.

16. The ventilation analysis system according to claim 15, wherein said breath flow dynamics sensor comprises a wireless breath flow dynamics sensor, a flow sensor, an acoustic sensor, a thermal sensor, a chest movement detector, a computer-aided video analyzer and/or a Doppler radar.

17. The ventilation analysis system according to claim 15, wherein said control logic is further configured to calculate an estimated End-Tidal $CO_2$ (EtCO2) value.

18. The ventilation analysis system according to claim 15, wherein said control logic is further configured to calculate an estimated minute $CO_2$ value.

19. The ventilation analysis system according to claim 15, wherein said $CO_2$ sensor comprises a wireless $CO_2$ sensor.

20. The ventilation analysis system according to claim 15, wherein said $CO_2$ sensor comprises a $CO_2$ sensor having a response time of 500 ms or more.

21. The ventilation analysis system according to claim 15, wherein said $CO_2$ sensor comprises a $CO_2$ sensor having a response time of 900 ms or more.

22. The ventilation analysis system according to claim 15, wherein said interface module is further configured to receive a Saturation of Peripheral Oxygen ($SpO_2$) signal.

23. The ventilation analysis system according to claim 22, further comprising a $SpO_2$ sensor configured to produce said $SpO_2$ signal.

* * * * *